United States Patent
Avachat et al.

(10) Patent No.: US 10,058,569 B2
(45) Date of Patent: Aug. 28, 2018

(54) LANTHANUM CARBONATE COMPOSITIONS

(71) Applicant: LUPIN LIMITED, Mumbai, Maharashtra (IN)

(72) Inventors: Makarand Krishnakumar Avachat, Maharashtra (IN); Nikhil P. Malewar, Maharashtra (IN); Anirudha B. Kute, Maharashtra (IN); Girish Purushottam Bang, Maharashtra (IN)

(73) Assignee: LUPIN LIMITED, Mumbai, Maharashtra (IN)

( * ) Notice: Subject to any disclaimer, the term of this patent is extended or adjusted under 35 U.S.C. 154(b) by 0 days.

(21) Appl. No.: 15/191,025

(22) Filed: Jun. 23, 2016

(65) Prior Publication Data
US 2016/0375055 A1 Dec. 29, 2016

(30) Foreign Application Priority Data
Jun. 24, 2015 (IN) .................... 2399/MUM/2015

(51) Int. Cl.
*A61K 33/24* (2006.01)
*A61K 9/00* (2006.01)
*A61K 9/16* (2006.01)

(52) U.S. Cl.
CPC .......... *A61K 33/24* (2013.01); *A61K 9/0053* (2013.01); *A61K 9/1623* (2013.01)

(58) Field of Classification Search
None
See application file for complete search history.

(56) References Cited

U.S. PATENT DOCUMENTS

| 5,968,976 | A * | 10/1999 | Murrer .................. A61K 33/24 424/715 |
| 7,179,486 | B1 | 2/2007 | Mulye |
| 7,381,428 | B2 | 6/2008 | Ferdinando et al. |
| 7,465,465 | B2 | 12/2008 | Haslam et al. |
| 8,263,119 | B2 | 9/2012 | Withington |
| 8,697,132 | B2 | 4/2014 | Withington et al. |
| 8,974,824 | B2 | 3/2015 | Amminabavi et al. |
| 8,980,327 | B2 | 3/2015 | Pierce et al. |
| 2006/0121127 | A1 * | 6/2006 | Ferdinando ......... A61K 9/0056 424/617 |
| 2012/0058200 | A1 * | 3/2012 | Muddasani ........... A61K 33/24 424/617 |
| 2012/0141581 | A1 * | 6/2012 | Withington ......... A61K 9/4858 424/452 |
| 2012/0219637 | A1 * | 8/2012 | Aniket ................ A61K 9/0056 424/617 |
| 2014/0178467 | A1 | 6/2014 | Withington et al. |
| 2015/0030695 | A1 | 1/2015 | Pierce et al. |

OTHER PUBLICATIONS

Alfred Martin et al.: "Physical Pharmacy", Physical Chemical Principles in the Pharmaceutical Sciences, Fourth Edition, Williams and Wilkins, Philadelphia, 2001, pp. 447-448.

* cited by examiner

*Primary Examiner* — Susan T Tran
*Assistant Examiner* — William A Craigo
(74) *Attorney, Agent, or Firm* — Merchant & Gould P.C.

(57) ABSTRACT

The invention relates to stable oral pharmaceutical compositions comprising lanthanum carbonate compounds and pharmaceutically acceptable excipients. The compositions of the present invention are formulated without the use of flow aids or lubricants. The compositions of the present invention have physical properties & flowability indicators comparable to that of the powders containing flow aids or lubricants and these compositions can be filled in sachets without any difficulty.

12 Claims, 2 Drawing Sheets

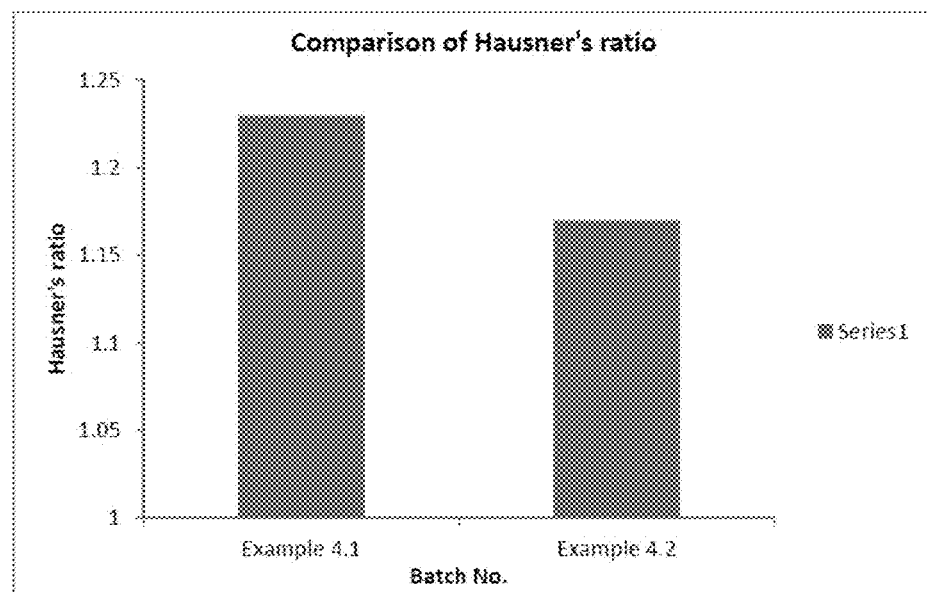
Figure 1: Effect of colloidal silicon dioxide on Hausner's ratio
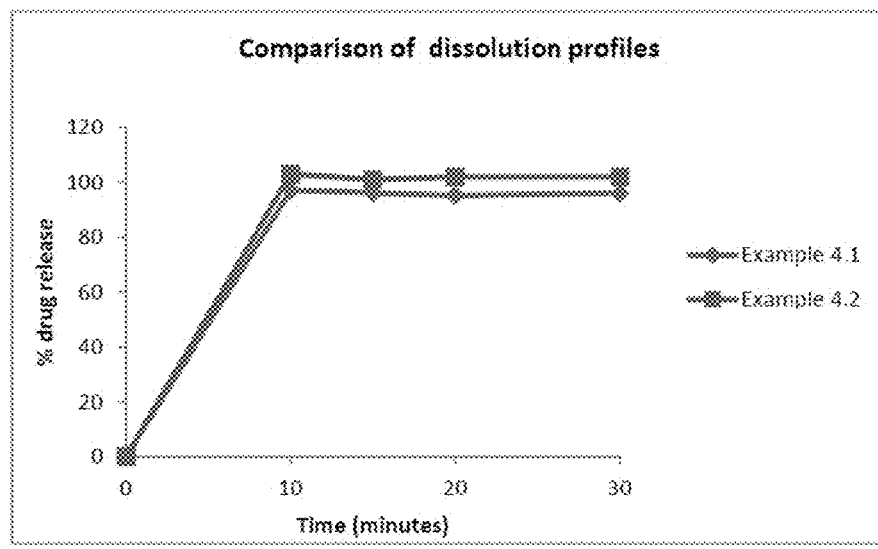
Figure 2: Effect of colloidal silicon dioxide on dissolution profiles of lanthanum carbonate formulations

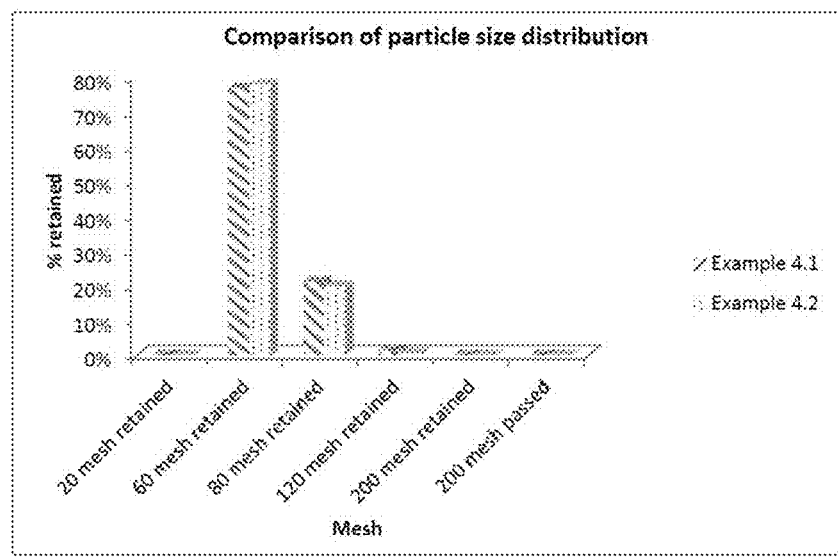
Figure 3: Comparative particle size distribution (sieve analysis) of powder formulations of examples 4.1 & 4.2.

LANTHANUM CARBONATE COMPOSITIONS

CROSS REFERENCE TO RELATED APPLICATIONS

This application claims benefit of Serial No. 2399/MUM/2015, filed 24 Jun. 2016 in India and which application is incorporated herein by reference. To the extent appropriate, a claim of priority is made to the above disclosed application.

FIELD OF THE INVENTION

The present invention relates to stable oral pharmaceutical compositions of lanthanum carbonate compounds and pharmaceutically acceptable excipients. The oral pharmaceutical compositions can be presented in the form of powders. The compositions of the present invention can be used in the treatment of patients suffering from hyperphosphatemia, chronic kidney disease (CKD), soft tissue calcification associated with CKD or secondary hyperparathyroidism.

BACKGROUND OF THE INVENTION

Powder flow is critical during formulation of powders, granules & during tableting as powders must flow easily and uniformly to ensure weight uniformity and production with consistent and reproducible properties. In order for powder to flow effectively, lubricants are essential because they reduce cohesiveness of the powder by reducing inter-particle friction and help the powder to flow without affecting dose uniformity, avoid picking, sticking, improper filling, clogging of equipment, improper emptying from sachets, capsules etc (Physical Pharmacy, Fourth Edition, Alfred Martin, Lippincott, Williams and Wilkins Philadelphia; 2001; Page 447-448). The most commonly used lubricants and flow aids are magnesium stearate, stearic acid salts and derivatives, talc & colloidal silicon dioxide. Lubricants, flow aids, glidants, anti-adherents are used interchangeably and have more or less the same purpose.

U.S. Pat. No. 7,381,428 describes a stabilized composition of lanthanum carbonate having 13.4-13.9% to 32.2-33.3% by weight of the composition as elemental lanthanum and excipients like stabilizing agent (dextrates), lubricants & glidants (like magnesium stearate, talc, polyethylene glycol, silica, colloidal silicon dioxide, hydrogenated vegetable oil, glyceryl behenate or glyceryl monostearate). Specification discloses lanthanum carbonate degrades to lanthanum hydroxycarbonate and the process is accelerated in presence of moisture/water and heat.

U.S. Pat. No. 7,465,465 describes lanthanum carbonate chewable tablets and powder formulations and states that lanthanum compounds such as lanthanum carbonate have poor flow characteristics and it represents a challenge while formulating compositions having a high drug load. The powder formulations contain the active along with pharmaceutically acceptable excipients which specifically include flow agents like silica, colloidal anhydrous silica, magnesium stearate, talc, polyethylene glycol, hydrogenated vegetable oils, glyceryl behenate & glyceryl monostearate. The flow agent is used in amounts from about 0.1% to about 5.0%. The patent advises against the method of wet granulation and drying as it may affect the hydration state of Lanthanum carbonate, an important aspect related to its biological properties. U.S. Pat. No. 8,263,119 describes a capsule encapsulating a powder composition of lanthanum carbonate and a lubricant such as talc and/or colloidal silicon dioxide. Dextrates is used as a diluent, colloidal silicon dioxide as flow aid and magnesium stearate as a lubricant. U.S. Pat. No. 8,697,132 & U.S. Pat. No. 8,980,327 describe an oral pharmaceutical powder containing lanthanum carbonate, dextrates, crospovidone, colloidal silicon dioxide and talc and states that the powder composition has similar plasma lanthanum carbonate concentration as that of a chewable tablet comprising lanthanum carbonate, dextrates, colloidal silicon dioxide and magnesium stearate. The formulation was optimized using various ingredients. It further states that lubricants prevent the formulation from sticking to the process equipment while flow aids help the formulation to flow freely during and after being processed. The lubricant amount can be from about 0.01% to about 0.05%, preferably from about 0.01% to about 0.04%, and most desirably from about 0.01% to about 0.03% by weight of the powder or the capsule contents of the formulation. The flow aid amount can be from about 0.1% to about 4%, preferably from about 0.1% to about 3%, and most desirably from about 0.1% to about 2% by weight of the powder or the capsule contents of the formulation. Examples state that lubricants when added lead to better flow properties. The patent lays emphasis on the fact that flow aids, lubricants and other excipients need to be thoroughly studied and optimized as they affect the dissolution of the final dosage form. Example 15 in the specification demonstrates the manufacture of unit dose by using a dosing auger of 8 mm and 60-70% of auger speed. U.S. Pat. No. 8,974,824 describes a wet granulated composition of lanthanum carbonate octahydrate devoid of monosaccharides and disaccharides. The specification discloses lubricants like calcium stearate, magnesium stearate, sodium lauryl sulfate, talc, mineral oil, stearic acid, zinc stearate, colloidal silicon dioxide, glyceryl behenate, polyethylene glycol, sodium stearyl fumarate, hydrogenated cottonseed oil, sodium benzoate, leucine or combinations thereof. US 2014/0178467 & US 2015/0030695 claim oral lanthanum carbonate compositions comprising specific excipients like dextrates, colloidal silicon dioxide, flow aids and lubricants. Impact of various ingredients (emphasis on lubricants and flow aids here) on the dissolution profile of the formulations were studied. The formulations were stored at 60° C. for a week. Specification indicates that extensive optimization studies were conducted for selecting lubricants and flow aids. Specification also mentions that lubricants stop the formulation from sticking to the process equipment while flow aids enable the formulations to flow freely while being processed, and colloidal silicon dioxides acts as a flow aid as well as lubricant.

U.S. Pat. No. 7,179,486 describes tablet compositions prepared by granulation. The patent emphasizes the importance of good flow properties to avoid improper filling of die cavities and entrapment and describes lubricants as typical ingredients of granules.

The prior art indicates that flow aids and lubricants are essential part of powder compositions especially for a compound having very poor flow properties like lanthanum carbonate. It lays special emphasis on these excipients for maintaining the ease of processing and overall quality of the product.

Flow aids and lubricants need to be thoroughly studied and their quantity needs to be optimized as they affect the dissolution of the final dosage form. Moreover a large number of excipients add to the bulk, preformulation study steps, processing steps and overall cost of the product. Thus, the more the excipients required, more is the cost as well as the manufacturing steps. Moreover, powders & granules require mechanical devices like auger for conveying them during filling operation & the process parameters of the conveyor auger like dimension and speed need to be optimized while filling into suitable containers. There is a need in the art to develop a better formulation of lanthanum carbonate which is cost effective and more precisely, uses limited number of excipients without compromising on the quality of the formulation.

There is a need in the art to develop formulations which provide powders & granules with desirable characteristics for formulation process and packaging and yet contain no lubricants or flow aids.

Lanthanum carbonate has a tendency to degrade to lanthanum hydroxycarbonate. The degradation process is accelerated by moisture and heat. The regulatory requirements preclude detectable decarboxylation for administration to patients. Thus there is a need in the art to develop lanthanum carbonate powder compositions that are stable against substantial decarboxylation to lanthanum hydroxycarbonate. We have surprisingly found that lanthanum carbonate compositions can be formulated without lubricants and/or flow aids. These formulations have flow properties comparable with that of compositions which contain flow aids and lubricants. It is a finding of the present invention that lanthanum carbonate compositions can be formulated using dextrates alone as excipient without the use of other additional excipients as necessitated by the prior art.

The present invention helps to reduce cost & save time as it reduces the time required for optimization of excipients like lubricants, flow aids or binders and reduces powder bulk.

SUMMARY OF THE INVENTION

The present invention relates to stable oral pharmaceutical compositions of lanthanum carbonate compounds. The oral pharmaceutical compositions of the present invention can be presented in the form of powders. Powders of the present invention are devoid of lubricants and flow aids.

The present invention eliminates a number of excipients used in the prior art.

BRIEF DESCRIPTION OF DRAWINGS

FIG. 1 shows the effect of colloidal silicon dioxide on Hausner's ratio.

FIG. 2 shows the effect of colloidal silicon dioxide on dissolution profiles of lanthanum carbonate formulations.

FIG. 3 shows comparative particle size distribution (sieve analysis) of powder formulations of examples 4.1 & 4.2.

DETAILED DESCRIPTION OF THE INVENTION

It is an object of the present invention to prepare a stable oral pharmaceutical powder composition comprising lanthanum carbonate and excipients without the use of lubricant and flow aids.

The present invention is based on the surprising finding that lanthanum carbonate powder compositions without lubricants and flow aids have flow properties comparable with that of powders formulated using lubricants and flow aids.

It is an object of the present invention to prepare a formulation which reduces cost & saves time, by reducing the time required for optimization of lubricants and flow aids, and thus reduces the powder bulk.

It is an object of the present invention to eliminate additional excipients thus reducing the number of steps for formulation.

It is an object of the present invention to provide powders & granules with desirable characteristics for formulation process and packaging and yet contain no lubricants or flow aids.

It is an object of the present invention to prepare stable oral powder composition of lanthanum carbonate with wet granulation technique without detectable amount of lanthanum hydroxycarbonate impurity. The present invention is based on the unexpected finding that powder compositions of lanthanum carbonate can be formulated without the use of lubricants or flow aids. This finding eliminates the need of rigorous studies involved in selection and optimization of such excipients, thereby eliminating the chances of alteration in dissolution properties. The formulations of the present invention provide a consistent dissolution profile before and after storage.

Oral Pharmaceutical Powders

The term 'oral pharmaceutical powders' herein is meant as powders for oral administration. Oral pharmaceutical powders of the present invention encompass granules, pellets, particles, aggregates and spheroids. The oral pharmaceutical powders of the present invention can be filled in sachets or capsules.

Oral pharmaceutical compositions of the present invention are devoid of lubricants and flow aids and yet are free flowing.

The method of making oral pharmaceutical powders of the present invention includes sieving the required ingredients, mixing them, adding the binder solution to granulate, drying the granules and optionally milling and/or sieving them.

The powders can be filled into sachets, capsules, stick packs, or rigid containers such as glass or plastic bottles or vials either as unit doses or as bulk quantities from which individual doses can be measured with a suitable measuring device using methods known to one of ordinary skill in the art. Each unit dose can contain from about 200 mg to about 2000 mg of elemental lanthanum as lanthanum carbonate. Preferably each sachet contains 250 mg, 500 mg, 750 mg or 1000 mg of elemental lanthanum as lanthanum carbonate.

Powders provide palatable alternatives to chewable tablet formulation. It is advantageous for patients suffering from kidney disease, wherein fluid intake needs to be regulated. Powders can be sprinkled onto the tongue or onto food.

The oral pharmaceutical powders and capsules of the present invention can be administered to treat a patient at risk of or suffering from hyperphosphatemia. It can further be used to treat a patient (1) at risk of or suffering from chronic kidney disease (CKD), (2) at risk of or suffering from soft tissue calcification associated with chronic kidney disease (CKD) or (3) at risk of or suffering from secondary hyperparathyroidism.

Lanthanum Carbonate and Lanthanum Carbonate Hydrate

"Lanthanum carbonate" as used herein encompasses hydrated forms of lanthanum carbonate having hydration state from 0 to 10 molecules of water per one molecule of lanthanum carbonate. The powder formulations of the invention contain lanthanum carbonate having the general formula $La_2(CO_3)_3 \cdot xH_2O$, wherein x has a value from 0 to 10. Preferably, x has a value from 2 to 6, more preferably from 2 to 4. Most preferably x has a value of 2. The amount of elemental lanthanum as lanthanum carbonate in the powder ranges from about 26 wt % to about 50 wt %, preferably from about 35 wt % to about 50 wt % and most preferably from about 40 wt % to about 50 wt % based on the total weight of the powder. The amount of elemental lanthanum in a sachet containing the lanthanum carbonate powder can range from 250 to 1000 mg. The amount can be 250 mg, 350 mg, 500 mg, 750 mg, or 1000 mg and preferably 750 mg to 1000 mg.

Additional Ingredients for Oral Pharmaceutical Powders

The present invention eliminates the need of using multiple additional excipients. The use of lubricants and flow aids is not necessitated by the present invention. Dextrates in appropriate quantity can act as diluent as well as binder. However, other excipients like flavors and sweeteners can be used.

Additional pharmaceutically acceptable ingredients that can be used for oral powders include diluents, binders, disintegrants, colors, flavors and sweeteners.

A binder can be added to the formulation in an amount from about 1 wt % to 10 wt %, preferably about 2 wt % to about 8 wt %, more preferably about 3 wt % to about 5 wt % based on the total weight of the powder contents of the formulation.

A diluent can be added to the formulation in an amount from about 5 wt % to about 50 wt % based on the total weight of the powder. The total diluent amount can be about 5 wt % to about 35 wt %, and preferably about 5 wt % to about 30 wt %, more preferably about 20 wt % to 30 wt % based on the total weight of the powder contents of the formulation.

Diluents include monosaccharide, disaccharide, mixture of saccharides like dextrates, calcium sulfate dihydrate, oligosaccharide, isomaltooligosaccharide, erythritol, polydextrose, dextrins, starch, maltodextrin, calcium lactate trihydrate, microcrystalline cellulose, hydrolyzed cereal solids, amylose, or glycine. One or more of these diluents can be present in the formulation.

Suitable monosaccharides for use in the formulation of the present invention include, but are not limited to, glyceraldehyde, erythrose, threose, ribose, lyxose, xylose, arabinose, allose, gulose, mannose, glucose, idose, galactose, altrose, dihydroxyacetone, erythrulose, ribulose, xyloketose, psicose, tagatose, sorbose, fructose, sorbitol, xylitol, inositol, erythritol, and mannitol in either the D- or L-configuration, including derivatives and analogs thereof. Suitable disaccharides for use in the present invention include, but are not limited to, sucrose, confectioner's sugar, or Nutab, lactose (including anhydrous lactose and lactose monohydrate), maltose, isomaltose, cellobiose, trehalose, maltitol, isomalt, lactitol, mixtures, derivatives, and analogs thereof. Furthermore, monosaccharides and disaccharides can be used in the same formulation.

The powders of the present invention are processable and conveyable without the use of flow aids and/or lubricants. The powders show comparable handling efficiency during processing and packaging to powder compositions which include flow aids and/or lubricants like colloidal silicon dioxide, and magnesium stearate or similar compositions containing talc, or other flow aids or lubricants known in the prior art. Moreover the cost of production is reduced due to less number of excipients and associated processing steps.

The packaging and processing of the prior art powders require the use of auger to assist in conveying. The auger needs to be optimized for dimensions and speed of rotation. The present invention eliminates the use of auger in processing and packaging. Thus the elimination of optimizing the auger functional parameters and the auger itself simplifies the process.

The powders of the invention demonstrate sufficient stability and comply with all the desired acceptance specifications. The powders exhibit acceptable dissolution profile, lanthanum assay and impurity levels over all the time points in the stability study programme.

EXAMPLES

Preparations of Lanthanum Carbonate Oral Powder

Example 1

| Ingredient | 750 mg/sachet | 1000 mg/sachet |
|---|---|---|
| Lanthanum carbonate dihydrate equivalent to 750/1000 mg elemental lanthanum | 1333.285 | 1777.713 |
| Dextrates, hydrated NF (intragranular) | 453.965 | 605.287 |
| Dextrates, hydrated NF (binder) | 69.750 | 93.000 |
| Purified water USP | Q.S | Q.S |
| Total weight | 1857.000 | 2476.000 |

Example 2

| Ingredient | 750 mg/sachet | 1000 mg/sachet |
|---|---|---|
| Lanthanum carbonate dihydrate equivalent to 750/1000 mg elemental lanthanum | 1333.285 | 1777.713 |
| Dextrates, hydrated NF (intragranular) | 430.865 | 574.487 |
| Dextrates, hydrated NF (binder) | 92.850 | 123.800 |
| Purified water USP | Q.S. | Q.S. |
| Total weight | 1857.000 | 2476.000 |

The manufacturing procedure for lanthanum carbonate powder formulation involves the following steps—
1. Lanthanum carbonate is sifted through 30 mesh S. S. sieve.
2. Dextrates, hydrated (intragranular) is sifted through 25 mesh S.S. sieve.
3. Approximately half quantity of step 1 material is loaded in rapid mixer granulator followed by step 2 materials and remaining quantity of step 1 material and is mixed for 15 minutes.
4. Binder solution is prepared by dissolving dextrates, hydrated (binder) in purified water.
5. Step 3 materials are granulated with solution of step 4 and extra purified water, if required, till a mass of suitable consistency is achieved.
6. The granules of step 5 are dried at 50±5° C. till % LOD is not more than 3%. The dried granules are sifted through 30 mesh S.S. sieve.
7. The step 6 materials are loaded in blender and mixed for 10 minutes at 5 rpm.
8. Finally the step 7 materials are filled in sachets.

Example 3

| Ingredient | 750 mg/sachet | 1000 mg/sachet |
|---|---|---|
| Lanthanum carbonate dihydrate equivalent to 750/1000 mg elemental lanthanum | 1333.285 | 1777.713 |
| Dextrates, hydrated NF | 523.715 | 698.287 |
| Purified water USP | Q.S. | Q.S. |
| Total weight | 1857.000 | 2476.000 |

The manufacturing procedure for lanthanum carbonate powder formulation involves the following steps—
1. Lanthanum carbonate is sifted through 40 mesh S.S. sieve and dextrates are sifted through 30 mesh S.S. sieve, separately.
2. The sifted material of step 1 is then added to rapid mix granulator and mixed for 15 min.
3. The mixture of step 2 is granulated with purified water, till a mass of suitable consistency is achieved.
4. The granules obtained in step 3 are dried at 50±5° C. till % LOD is not more than 3%.
5. The dried granules are then sifted through 30 mesh S.S. sieve and filled in sachets.

Example 4: Effect of Colloidal Silicon Dioxide on Flow Properties of Lanthanum Carbonate Powder Formulations

Example 4.1

| Ingredient | 750 mg/sachet | 1000 mg/sachet |
|---|---|---|
| Lanthanum carbonate dihydrate equivalent to 750/1000 mg elemental lanthanum | 1333.285 | 1777.713 |
| Dextrates, hydrated NF (intragranular) | 453.965 | 605.287 |
| Dextrates, hydrated NF (binder) | 69.750 | 93.000 |
| Colloidal silicon dioxide | — | — |
| Purified water USP | Q.S. | Q.S. |
| Total weight | 1857.000 | 2476.000 |

Example 4.2

| Ingredient | 750 mg/sachet | 1000 mg/sachet |
|---|---|---|
| Lanthanum carbonate dihydrate equivalent to 750/1000 mg elemental lanthanum | 1333.285 | 1777.713 |
| Dextrates, hydrated NF (intragranular) | 455.465 | 607.287 |
| Dextrates, hydrated NF (binder) | 69.750 | 93.000 |
| Colloidal silicon dioxide | 16.500 | 22.000 |
| Purified water USP | Q.S. | Q.S. |
| Total weight | 1875.000 | 2500.000 |

The formulations of Example 4.1 and 4.2 were manufactured using the process described for Examples 1 & 2 except Example 4.2 contained colloidal silicon dioxide. These formulations were studied for the effect colloidal silicon dioxide on flow properties, physical parameters, dissolution properties and content uniformity. The results are tabulated below.

TABLE 1

Comparative analysis of physical properties of powders of Example 4.1 and 4.2.

| | | Physical properties of blend | |
|---|---|---|---|
| | Parameters | Example 4.1 Observations | Example 4.2 Observations |
| | Description | White to off-white powder | White to off-white powder |
| | Bulk density (g/mL) | 0.96 | 0.95 |
| | Tapped density (g/mL) | 1.18 | 1.11 |
| | Carr's Index | 18.64 | 14.41 |
| | Hausner's Ratio | 1.23 | 1.17 |
| Sieve analysis | 20 mesh retained | 0% | 0% |
| | 60 mesh retained | 77.03% | 78% |
| | 80 mesh retained | 21.19% | 20% |
| | 120 mesh retained | 1.29% | 0.6% |
| | 200 mesh retained | 0% | 0% |
| | 200 mesh passed | 0% | 0% |
| Sachet filling | Uniformity of fill weight: 1.857 g ± 3% of theoretical weight (1.801 g to 1.912 g) | 1.824 g to 1.901 g | — |
| | Weight of powder filled in 10 sachets: 18.570 g ± 2% of target fill weight (18.199 g to 18.941 g) | 18.410 g to 18.698 g | — |
| Sachet filling | Uniformity of fill weight: 1.875 g ± 3% of theoretical weight (1.819 g to 1.931 g) | — | 1.838 g to 1.929 g |
| | Weight of powder filled in 10 sachets: 18.750 g ± 2% of target fill weight (18.375 g to 19.125 g) | — | 18.98 g to 19.10 g |
| | Assay | 100.4% | 98.7% |
| Uniformity of dosage units (By weight variation) | Mean | 101.5% | 99.7% |
| | Min | 100.3% | 98.9% |
| | Max | 102.4% | 100.2% |
| | Acceptance value | 2 | 1 |
| Dissolution: Media: 0.25N HCl, Volume: 900 mL, Apparatus: Paddle, 25 RPM | Time (minutes) | Drug release (%) | |
| | 10 | 97 | 103 |
| | 15 | 96 | 101 |
| | 20 | 95 | 102 |
| | 30 | 96 | 102 |
| % Lanthanum Hydroxycarbonate content (By PXRD) | | Below Detection Level | Below Detection Level |

As is indicated from the above table & FIGS. 1 & 3 the results obtained by comparative analysis shows that the powder which is devoid of colloidal silicon dioxide has flow properties and content uniformity comparable with that of powder containing colloidal silicon dioxide. This signifies that the powder formulations of lanthanum carbonate using dextrates and without colloidal silicon dioxide can be processed efficiently during formulation and packaging. Moreover the level of lanthanum hydroxyl carbonate is below the detection level.

The flow properties of the powder can be measured using the Carr's index and Hausner's ratio. Carr's index (CI) is the measure of the powder bridge strength and stability, whereas the Hausner's ratio (HR) relates to the interparticulate friction. The flow properties of the powder can be closely estimated based on these two indices. Lower values of these indices indicate better flow properties. A CI of <10 or HR<1.11 indicates "excellent" flow, whereas CI>38 or HR>1.60 is considered "very very poor". The flow property representation by various CI and HR values is tabulated below.

TABLE 2

Flow property characters in relation with Hausner's Ratio & Carr's Index

| CI value | HR value | Flow property character |
|---|---|---|
| <10 | <1.11 | Excellent |
| 11-15 | 1.12-1.18 | Good |
| 16-20 | 1.19-1.25 | Fair |
| 21-25 | 1.26-1.34 | Passable |
| 26-31 | 1.35-1.45 | Poor |
| 32-37 | 1.46-1.59 | Very poor |
| >38 | >1.60 | Very very poor |

The Carr's index and Hausner's ratio of the two powder formulations have comparable values indicating the flow properties of both the powders are similar as indicated by FIG. 1.

TABLE 3

Dissolution study of lanthanum carbonate powder compositions

| Time | Drug release (%) | |
|---|---|---|
| (minutes) | Example 4.1 | Example 4.2 |
| 0 | 0 | 0 |
| 10 | 97 | 103 |
| 15 | 96 | 101 |
| 20 | 95 | 102 |
| 30 | 96 | 102 |
| F2 value | 60.65 | |

The comparative dissolution study of lanthanum carbonate powder compositions described in Example 4.1 and Example 4.2 was carried out using the paddle apparatus using 900 ml of 0.25 N HCl as media. The dissolution studies were carried out at 25 rpm. The comparative dissolution profiles of the compositions were calculated as % drug release and are described in FIG. 2. The dissolution profiles of Example 4.1 & 4.2 are similar, as is indicated by the F2 value and FIG. 2.

Example 6: Stability Studies of Lanthanum Carbonate Oral Powder

The lanthanum carbonate oral powder of Example 1 was studied for stability by storing at 25±2° C. & 60±5% RH. The stored samples were analyzed for lanthanum content, moisture content, dissolution and lanthanum hydroxyl carbonate content before storing and at the intervals of 3, 6 & 9 months from storage. The results are depicted as below:

TABLE 4

Stability data of 1000 mg/sachet

| Tests | Specifications | Initial | 3 Month | 6 Month | 9 Month |
|---|---|---|---|---|---|
| Description | White to Off-white powder | Off-white powder. | White powder. | White powder. | White powder. |
| LOD (105° C. for 3 hrs) | NMT 7% w/w | 2.6 | 2.6 | 2.5 | 2.3 |
| Dissolution (%) (By Titrimetry) Apparatus: Paddle, 25 RPM, 900 ml 0.25N HCl, 30 min | NLT 80Q of the labelled amount of lanthanum dissolved in 30 min | 96 (93-97) | 101 (99-102) | 97 (95-99) | 100 (98-101) |
| Assay (mg) (By Titrimetry) Apparatus | 900.00 mg to 1100.00 mg (90.0% to 110.0% of label claim) | 1009 (100.9) | 1027.17 (102.7) | 972.62 (97.3) | 986.34 (98.6) |
| Lanthanum Hydroxy carbonate content Form I & II) By PXRD Method) (%) | NMT 5% | BDL | BDL | BDL | BDL |
| Remark | | Passes | Passes | Passes | Passes |

NMT—Not More Than
NLT—Not Less Than
BDL— Below Detection Limit

TABLE 5

Stability data of 750 mg/sachet

| Tests | Specifications | Initial | 3 Month | 6 Month | 9 Month |
|---|---|---|---|---|---|
| Description | White to Off-white powder | Off-white powder. | White powder. | White powder. | White powder. |
| LOD (105° C. for 3 hrs) | NMT 7% w/w | 2.5 | 2.7 | 2.1 | 2.0 |
| Dissolution (%) (By Titrimetry) Apparatus: Paddle, 25 RPM, 900 ml 0.25N HCl, 30 min | NLT 80Q of the labelled amount of lanthanum dissolved in 30 min | 95 (94-96) | 98 (96-101) | 98 (97-99) | 101 (99-103) |
| Assay (mg) (By Titrimetry) Apparatus | 900.00 mg to 1100.00 mg (90.0% to 110.0% of label claim) | 746.55 (99.5) | 754.93 (100.7) | 757.26 (101) | 746.2 (99.5) |
| Lanthanum Hydroxy carbonate content Form I & II) By PXRD Method) (%) | NMT 5% | BDL | BDL | BDL | BDL |
| Remark | | Passes | Passes | Passes | Passes |

NMT—Not More Than
NLT—Not Less Than
BDL—Below Detection Limit

The stability studies clearly indicate that the samples at various time intervals meet the desired specifications. The lanthanum hydroxy carbonate content of the composition is below quantification limit as is evidenced by the stability data. Thus, the lanthanum carbonate oral powders of Example 1 demonstrate the required stability.

We claim:

1. A stable oral pharmaceutical powder composition consisting of (1) lanthanum carbonate, lanthanum carbonate hydrate, or a combination thereof, and (2) dextrates, wherein the stable pharmaceutical composition has Carr's index value less than 25 or Hausner's ratio value less than 1.34.

2. The powder composition of claim 1 wherein the composition has lanthanum hydroxy carbonate content below quantifiable limit.

3. The powder composition of claim 1, wherein the lanthanum carbonate or lanthanum carbonate hydrate has the formula: $La_2(CO_3)_3 \cdot nH_2O$ wherein n has a value from 0 to 10.

4. The powder composition of claim 3, wherein n has a value from 2 to 6.

5. The powder composition of claim 1 wherein the composition is filled in sachets or capsules.

6. The powder composition of claim 1, wherein dextrates act as diluent and binder.

7. The powder composition of claim 6 wherein the binder concentration of dextrates is about 3 to about 5 weight %.

8. The powder composition of claim 6 wherein the diluent concentration of dextrates is about 20 to about 30 weight %.

9. The powder composition of claim 1 wherein the powder has Carr's index of less than 21.

10. The powder composition of claim 1 wherein the powder has Hausner's ratio of less than 1.25.

11. The powder composition of claim 1, wherein the composition is prepared by wet granulation.

12. The powder composition of claim 11 wherein the wet granulation method comprises forming a mixture by dry mixing of a first portion of a dextrates with lanthanum carbonate, and adding a second portion of the dextrates to the mixture, wherein the second portion of the dextrates is in the form of a solution or dispersion; drying and sifting the resulting granules.

* * * * *